United States Patent [19]
Easey et al.

[11] Patent Number: 5,544,447
[45] Date of Patent: Aug. 13, 1996

[54] CHEMICAL GROW BAG FOR ROOT GROWTH CONTROL AND CONTAINMENT

[76] Inventors: Norman Easey, 7853 S. Leewynn Ct., Sarasota, Fla. 34240; John Conroy, 1913 SE. 12th St., Cape Coral, Fla. 33990

[21] Appl. No.: 520,131

[22] Filed: Aug. 28, 1995

Related U.S. Application Data

[63] Continuation-in-part of Ser. No. 26,359, Jul. 26, 1994.

[51] Int. Cl.⁶ ........................................................ A01G 9/02
[52] U.S. Cl. .......................... 47/66; 47/39; 47/73; 47/76; 47/78; D8/1
[58] Field of Search ..................... 47/66 B, 66 R, 47/73 R, 76 R, 78 F, 76 WB, 39 P; D8/1

[56] References Cited

U.S. PATENT DOCUMENTS

| | | | |
|---|---|---|---|
| 3,211,404 | 10/1965 | Edmiston | 47/39 P |
| 4,096,662 | 6/1978 | Anderson | 47/76 R |
| 5,181,952 | 1/1993 | Burton | 47/9 S |
| 5,311,700 | 5/1994 | Thomas | 47/76 WB |

FOREIGN PATENT DOCUMENTS

| | | | |
|---|---|---|---|
| 384446 | 8/1990 | European Pat. Off. | 47/78 F |
| 153238 | 4/1938 | Germany | 47/78 F |
| 2744143 | 4/1979 | Germany | 47/78 F |

*Primary Examiner*—Henry E. Raduazo
*Attorney, Agent, or Firm*—Franklin J., P.E. Cona

[57] ABSTRACT

A root control and containment system for holding and growing a plant in a cavity in the earth for controlling and containing vertical and horizontal root growth is disclosed. The system includes a vessel having upstanding sidewalls and a base therebelow and an open top thereabove. A root inhibiting carbon bound material is in chemical communication with the vessel and stores and releases the root inhibiting carbon bound materials over protracted periods of time. The root inhibiting carbon bound material is disposed in a discrete pattern relationship on an inner surface of the sidewalls and the base. The controlled release of the carbon bound material rejects lateral root growth therethrough the wall and vertical root growth therethrough the base of the vessel. An arcuate collar is attached to an upper edge of the sidewall of the vessel and is disposed above the surface of the earth surrounding the cavity for rapid identification of the cavity by field personnel when performing field tasks. A cradle is adapted for congruent residence inside the vessel and is in removal engagement with the sidewalls and the base of the vessel. The cradle is vertically disposed and has a plurality of rings horizontally disposed in a spaced apart relationship. A plurality of lifting ears are disposed on an upper ring thereof for removing the plant safely when desired.

30 Claims, 12 Drawing Sheets

CHEMICAL GROW BAG FOR ROOT GROWTH CONTROL AND CONTAINMENT

This application is a Continuation-in-Part of the application Ser. No. 29/026,359, filed Jul. 26, 1994, now pending.

BACKGROUND OF THE INVENTION

Field of the Invention

The present invention relates to a system of controlling plant root growth in nursery operations, and more particular to releasing carbon bound root inhibiting materials in a vessel formed for containing all root growth and branching within the vessel.

It is well known in the art to grow nursery stock such as trees in containers above ground until the plants are mature enough to be transplanted. The growth of plants in containers involves a high degree of mortality due to high summer temperatures that reduce plant growth and low winter temperatures that often kill the roots of the plant in the vessel. Growing nursery stock above ground in containers is also susceptible to high winds and being blown over by those high winds and suffering catastrophic damage. Accordingly, the growth of nursery stock such as trees in the ground is desirable where the surrounding soil insulates the roots from the temperature extremes of the summer and winter and also maintains the plant in an upright position during high wind events. However, planting nursery stock below ground leads to difficulties when transplantation is desired. Previous efforts have been directed to minimizing the lateral root growth by the use of various root control bags that allow penetration of the walls of the bag and offer a convenient cut off point for the nurseryman when removing the plant from the ground. The severing of plant roots for transplantation is an inexact art. Many plants suffer a premature death due to the nurseryman making a mistake in judgement and severing vital roots as part of the overall trimming of the root ball before transplantation to the final site. Severing the vital roots causes the tree to become dead-upon-arrival at the transplantation site.

A system is needed to eliminate the decision making as to which plant roots to sever. Therefore it is an object of this invention to provide a root control system that contains all of the roots of the plant within a vessel in the ground and eliminates the decision to trim the roots on the part of the nurseryman.

Also, the planting of nursery stock in-ground and the later removal of the mature tree is time consuming and expensive process. A tree that is destroyed by excessive root trimming must be replaced by another live tree. A dead tree or nearly dead tree increases the landscaping cost to the final user. Therefore, a system that increases the survival rate of transplanted trees will reduce the unit cost of each individual tree to the consumer.

Description of the Background Art

Throughout the United States steps are being taken to improve root control and containment systems for holding and growing a plant in a cavity in the earth that successfully controls the vertical and horizontal root growth of the plant.

U.S. Pat. No. 5,116,414 issued to Burton et al. discloses a method of releasing a carbon bound root retardant chemical over many years. Patent '414 teaches the "dwarfing" of a tree or a shrub by retarding root growth.

U.S. Pat. No. 5,181,952 issued to Burton et al. discloses a method of fabricating a sheet having a carbon bound root inhibiting chemical with the sheet being non-woven for inhibiting root growth in nuclear plants and around chemical and sewer pipes. Patent '952 teaches placing the carbon bound root inhibiting material on a sheet.

U.S. Pat. No. 5,139,566 issued to Zimmerman discloses a method of fabricating a geotextile sheet having spaced apart buttons on an interior surface thereof for releasing the root inhibiting agents contained in the buttons into the soil over a protracted period of time. Patent '566 teaches a method to make the geotextile sheet and form the button in a spaced apart relationship on the sheet.

U.S. Pat. No. 4,959,865 issued to Whitcomb et al. discloses a container suitable for growing a transplantable tree.

U.S. Pat. No. 3,711,992 issued to Martin discloses an apparatus for securing transplantable trees.

U.S. Pat. No. 4,019,279 issued to Moorman et al. discloses a planter for protecting roots of a tree from cracking nearby sidewalks.

U.S. Pat. No. 3,634,970 issued to Williams discloses a wrapper for the earth ball of the tree to be moved.

U.S. Pat. No. 4,884,367 issued to Lawton discloses a root bag formed of a non-woven fabric material for containing tree roots during in-ground alteration and transplantation in nursery operations.

U.S. Pat. No. 5,167,092 issued to Reiger discloses a fabric container for controlling root growth of nursery stock prior to transplantation.

U.S. Pat. No. 4,574,522 issued to Reiger et al. discloses a root control bag for transplantation of nursery stock.

None of these previous efforts, however, provide the benefits intended with the present invention. Additionally, prior techniques do not suggest, the present inventive combination of component elements as disclosed and claimed herein. The present invention achieves its intended purposes, objectives and advantages over the prior art devices through a new, useful and unobvious combination of component elements, which is simple to use, with the utilization of a minimum number of functioning parts, at a reasonable cost to manufacture, assemble, test and by employing only readily available material.

What is needed is a chemical root control and containment system that allows all of the roots to grow within the confines of the vessel and also provide a method of removing the plant and its roots without damaging the health of the plant/root system and that is easy to use with conventional nursery field equipment.

Therefore it is an object of this invention to provide a chemical root control and containment system that maintains all of the root structure within the confines of the vessel while allowing the nurseryman an easy method to remove the tree/root system from the vessel without any adverse deterioration of the tree/root system.

It is a further object of this invention to provide a chemical root control and containment system for nursery operations that will significantly reduce the labor associated with in-ground cultivation and transplantation of plants when the desired maturity level has been reached.

It is a further object of the invention provide a chemical root control and containment system which emits carbon bound root inhibiting materials into the surrounding growing medium of the nursery root stock.

It is still yet another object of the invention to provide a chemical root control and containment system that restricts lateral root growth and promotes root branching within the volume of the vessel.

It is still yet another object of the invention to provide a chemical root control and containment system that can be readily incorporated into existing nursery operations for cultivation and transplantation operations.

It is yet another object of the invention to provide a method of planting nursery stock in a readily transplantable vessel and providing for a method of removing the nursery stock when the desired size and caliper is reached.

A final object of this invention to be specifically enumerated herein is to provide a chemical root control and containment system in accordance with the preceding objects and which will conform to conventional forms of manufacture, be of simple construction and easy to use so as to provide a device that would be economically feasible, long lasting and relatively trouble free in operation.

Although there have been many inventions related to root control and containment systems, none of the inventions have become sufficiently compact, low cost and reliable enough to become commonly used. The present invention meets the requirements of the simplified design, compact size, low initial cost, low operating cost, ease of installation and maintainability, and minimal amount of training to successfully employ the invention.

The foregoing has outlined some of the more pertinent objects of the invention. These objects should be construed to be merely illustrative of some of the more prominent features and applications of the intended invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description of the preferred embodiments in addition to the scope of the invention defined by the claims taken in conjunction with the accompanying drawings.

SUMMARY OF THE INVENTION

The invention is defined by the appended claims with the specific embodiment shown in the attached drawings. For the purpose of summarizing the invention, the invention may be incorporated into a root control and containment system for holding and growing a plant in a cavity in the earth for controlling vertical and horizontal root growth. The invention includes a vessel having upstanding sidewalls and a base therebelow and an open top thereabove. The sidewalls and base have a smooth inner and outer surface. A root inhibiting carbon bound material is in chemical communication with the vessel and stores and releases the root inhibiting carbon bound material over protracted periods of time. The slow release of the material rejects lateral root growth therethrough the wall and rejects vertical root growth therethrough the base of the vessel while the plant stock matures and grows. An arcuate collar is attached to an upper edge of the sidewalls of the vessel and is fabricated from a substance that resists ultraviolet deterioration. An upper portion of the arcuate collar is disposed above the surface of the earth and surrounds the cavity for rapid identification of the cavity by field personnel when performing transplantation of the tree. The upper portion also provides for indexing the invention to the correct height and to protect the below fabric from ultraviolet degradation. A cradle adapted for congruent residence inside the vessel is in removal engagement with the sidewalls and the base of the vessel. Further, the cradle has a plurality of rings horizontally disposed in a spaced apart relationship. A plurality of lifting ears are disposed on an upper ring thereof for urging removal of the tree when desired. The root inhibiting carbon bound material is contained in a plurality of studs that are disposed in a discrete pattern relationship on an inner surface of the walls and the base.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent structures do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
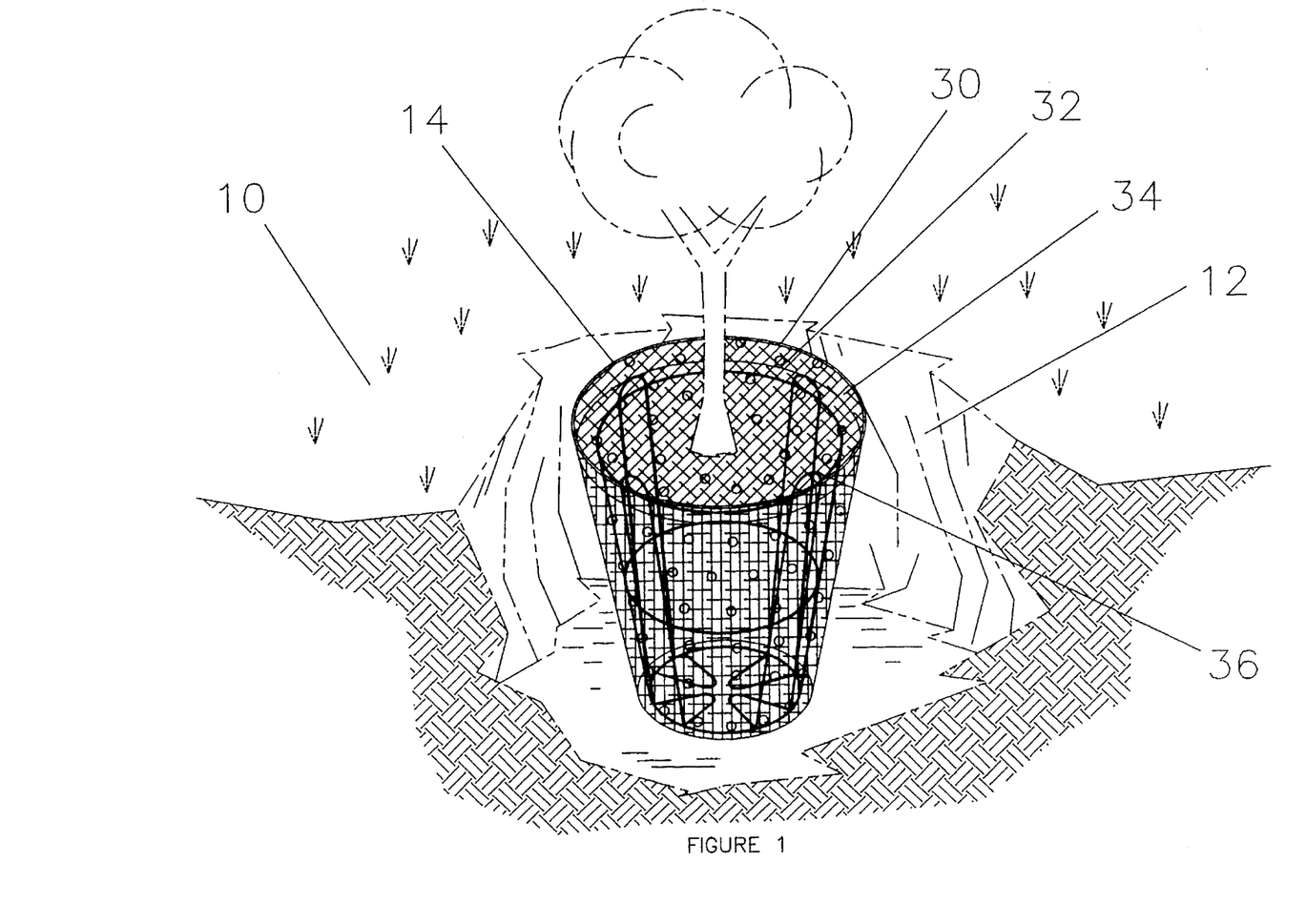
FIG. 1 is a pictorial representation of the preferred embodiment of the invention.
Figure 2:
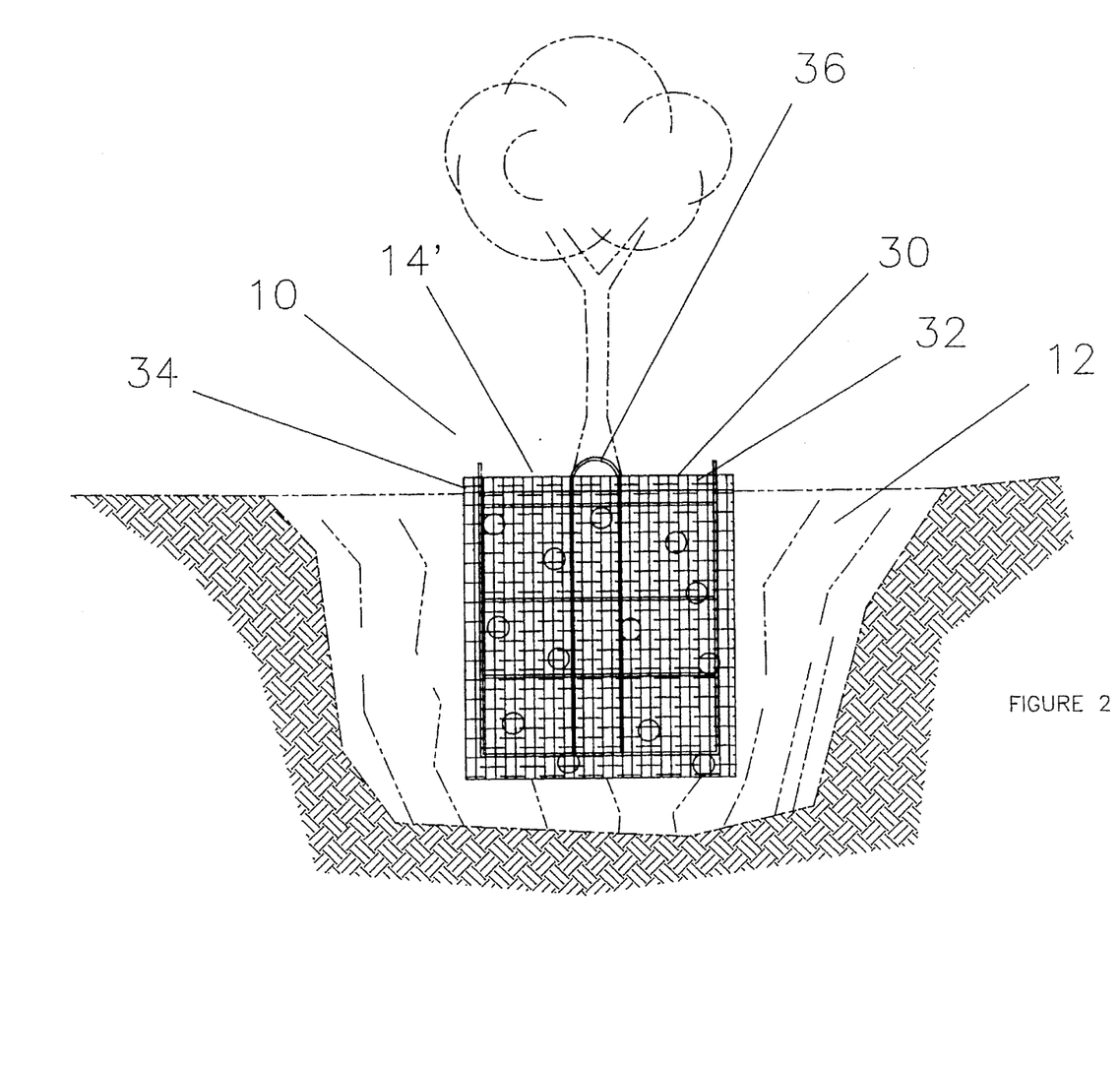
FIG. 2 is a pictorial representation of the cylindrical embodiment of the invention.
Figure 3:
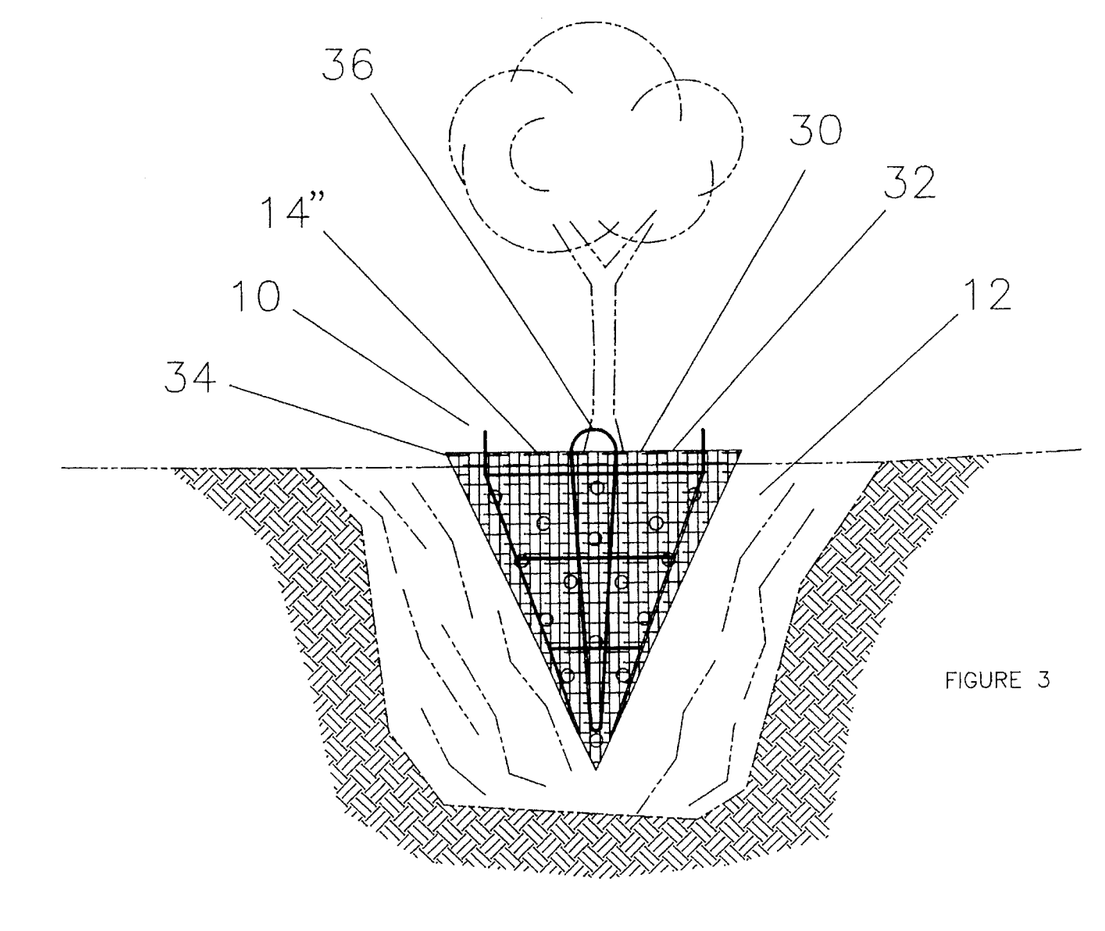
FIG. 3 is a pictorial representation of the conical shaped embodiment of the invention showing the geotextile sidewall material having the chemical nodules in a spaced apart relationship.
Figure 4:
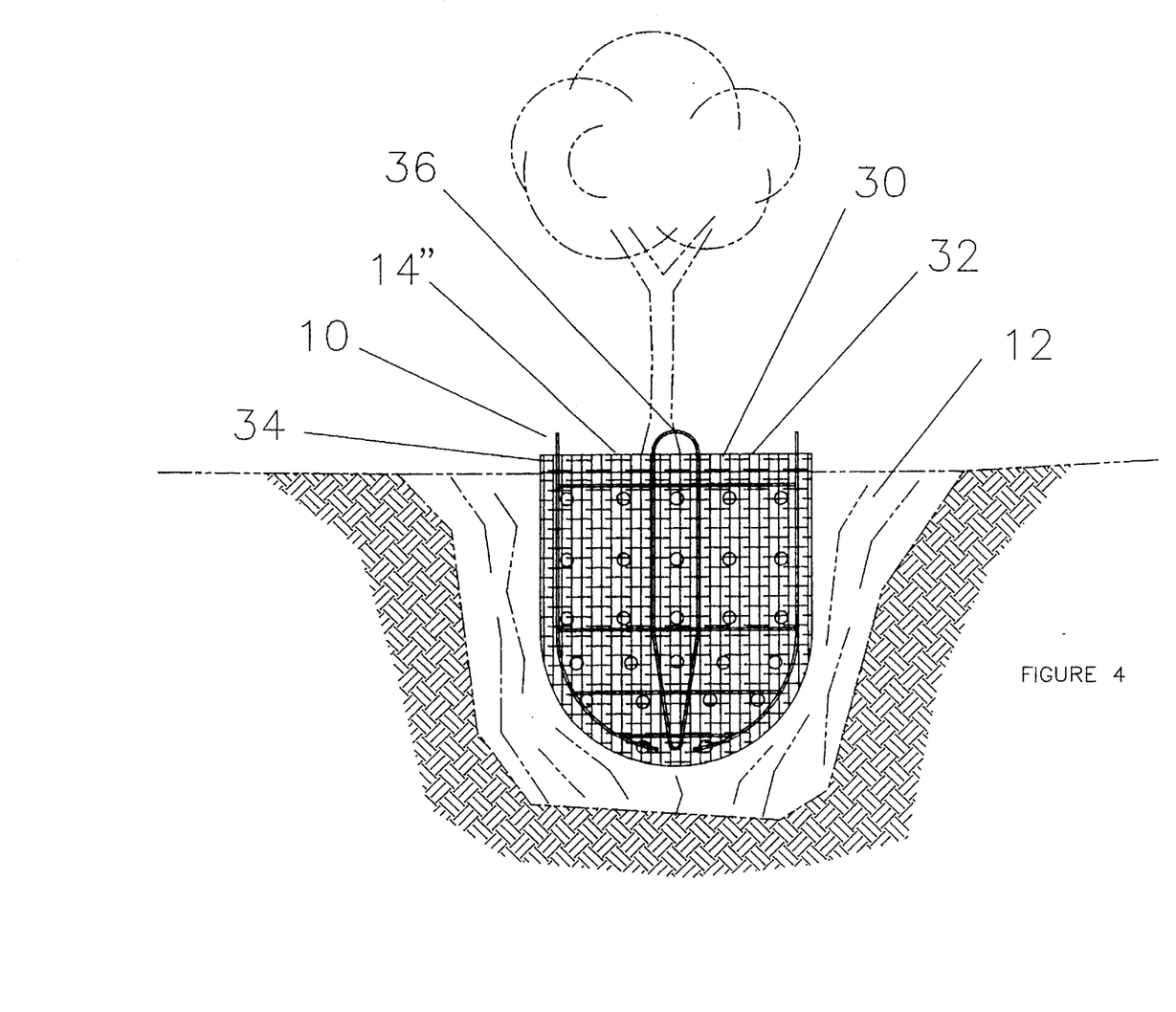
FIG. 4 is a pictorial representation of the arcuate shaped or bullet nosed embodiment of the invention.

Referring generally to FIG. 1, the invention 10 is a root control and containment system for holding and growing a plant in a cavity 12 in the earth for controlling vertical and horizontal root growth. The invention 10 comprises a vessel 14 with upstanding sidewalls 16, 16' and a base 18 therebelow and an open top 20 thereabove. The sidewalls 16, 16' and base 18 have a smooth inner 22, 22' and outer surface 24, 24'. A root inhibiting carbon bound material 26 is in chemical communication with the vessel 14 and stores and releases the root inhibiting carbon bound material 26 over protracted periods of time. The released carbon bound material 26 rejects lateral root growth therethrough the sidewalls 16, 16' and rejects vertical root growth therethrough the base 18 of the vessel 14 for extremely long periods of time. The invention will make planting and transplantation of plant stock an easy operation and dramatically reduce transplant mortality rates by eliminating shock caused when plant roots are inadvertently severed during plant removal operations.

Figure 7:
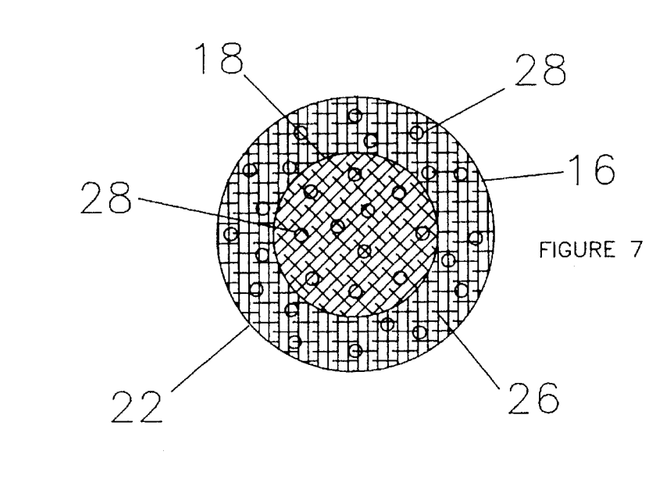
FIG. 7 the top plan view of the preferred embodiment of the invention.
Figure 8:
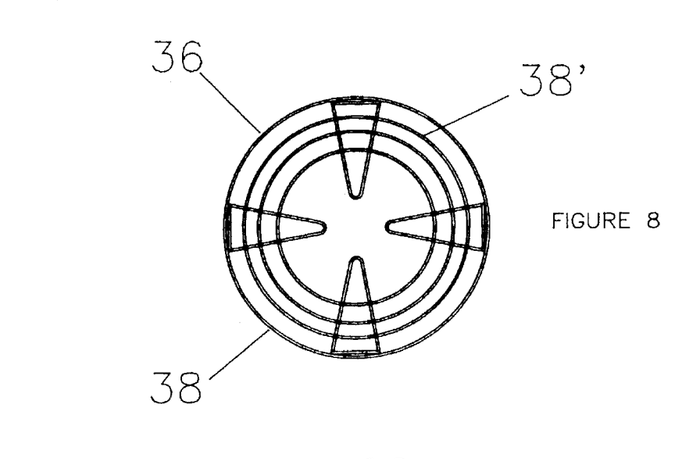
FIG. 8 is a top plan view of the wire basket component of the invention as shown in FIG. 1.
Figure 9:
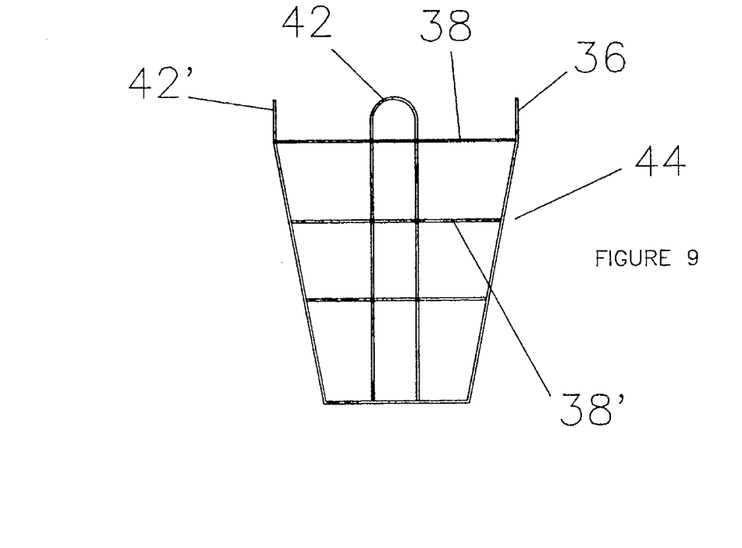
FIG. 9 is a front elevational view of the wire basket component of the invention disclosing the lifting lug attachments as shown in FIG. 1.
Figure 10:
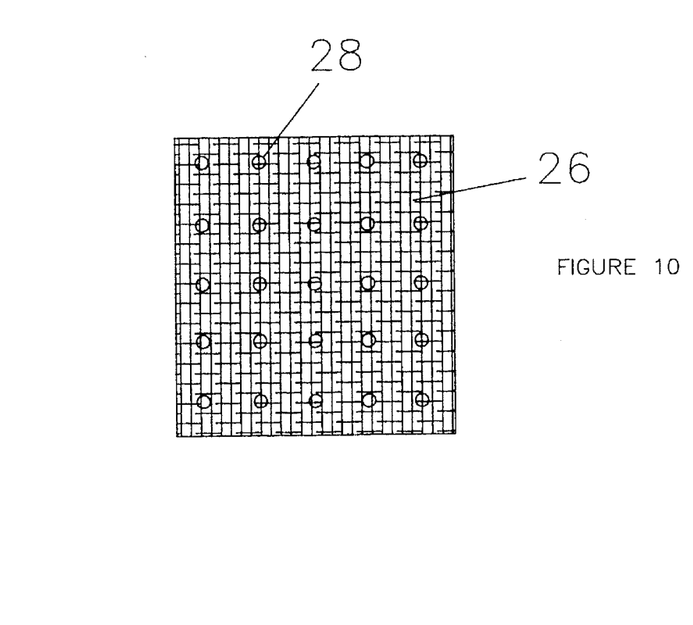
FIG. 10 is a front elevational view of the cylindrical embodiment of the invention as shown in FIG. 2.
Figure 11:
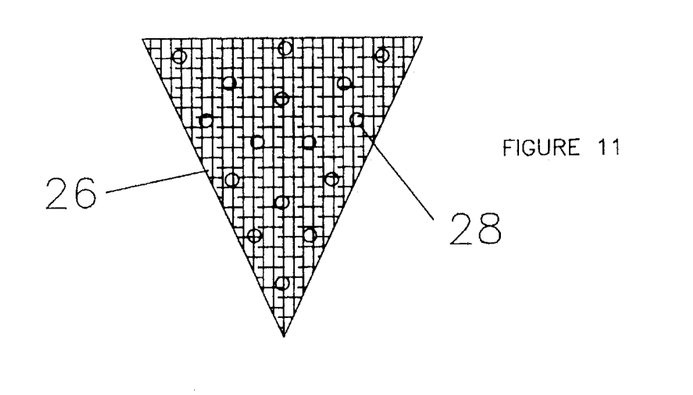
FIG. 11 is a front elevational view of the triangular conical shaped embodiment of the invention as shown in FIG. 3.
Figure 12:
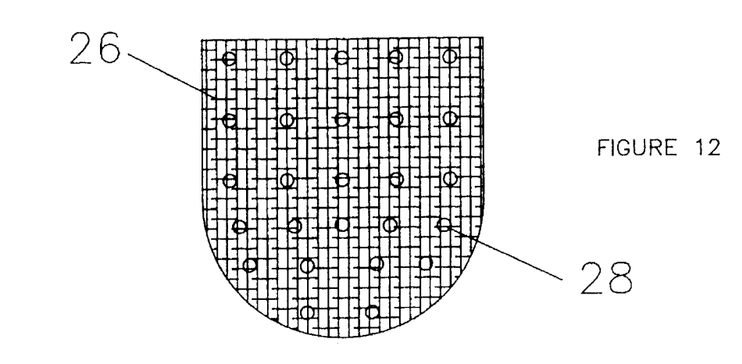
FIG. 12 is a front elevational view of the arcuate shaped, bullet nosed embodiment of the invention as shown in FIG. 4.
Figure 13:
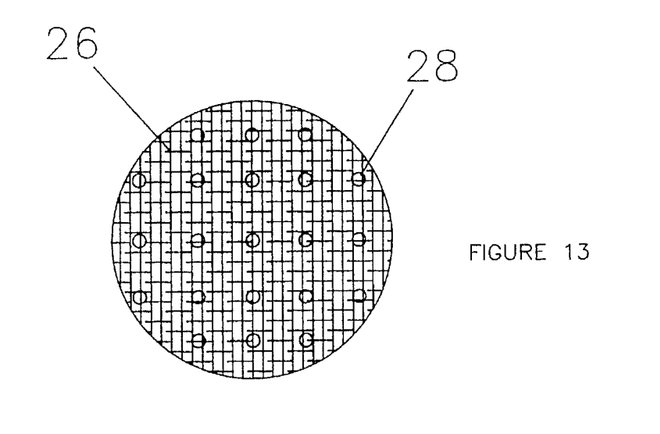
FIG. 13 is a top plan view of the cylindrical shaped embodiment of the invention as shown in FIG. 2.
Figure 14:
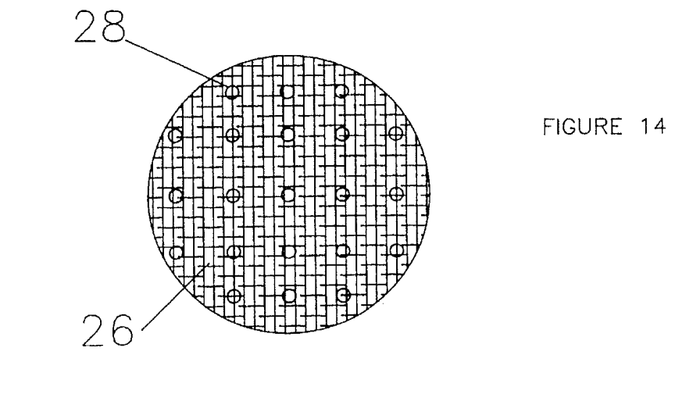
FIG. 14 is a top plan view of the conical shaped embodiment of the invention as shown in FIG. 3.
Figure 15:
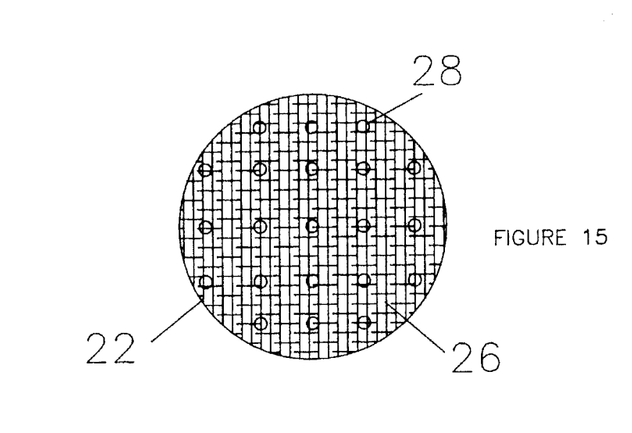
FIG. 15 is a top plan view of the bullet nosed embodiment of the invention as shown in FIG. 4.
Figure 16:
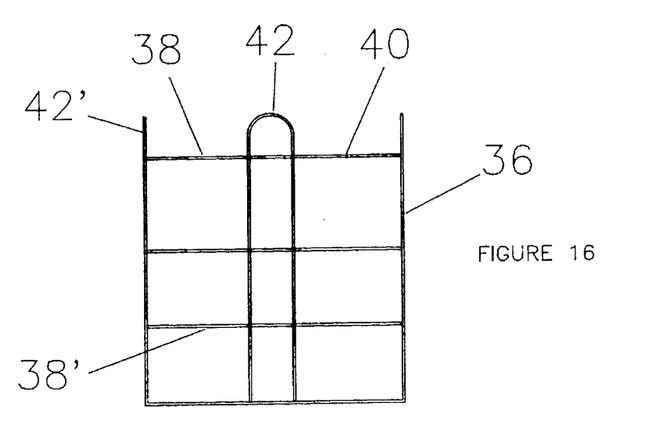
FIG. 16 is a front elevational view of the wire basket component of the invention for the cylindrical shaped embodiment of the invention as shown in FIG. 2.
Figure 17:
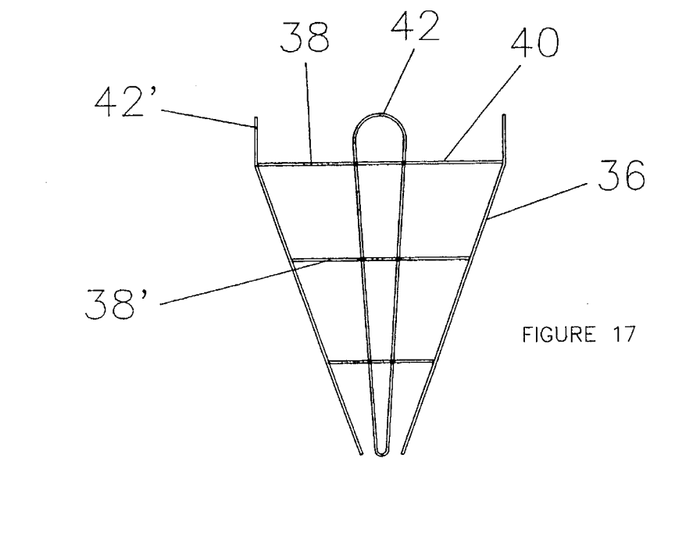
FIG. 17 is a front elevational view of the wire basket component for the conical shaped embodiment of the invention as shown in FIG. 3.
Figure 18:
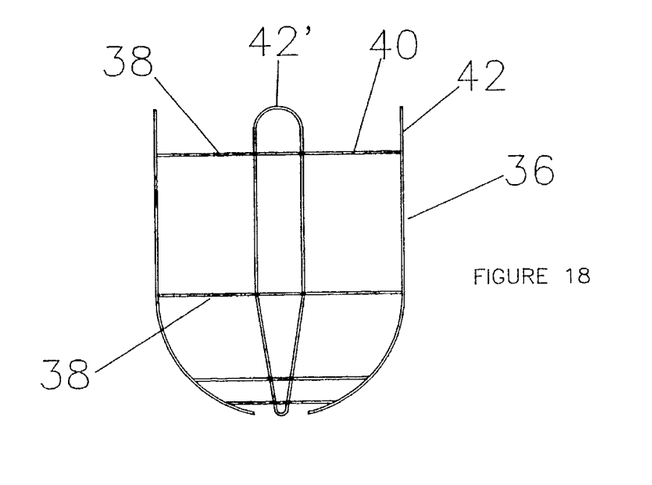
FIG. 18 is a front elevational view of the wire basket component for the arcuate shaped, bullet nosed embodiment of the invention as shown in FIG. 4.
Figure 19:
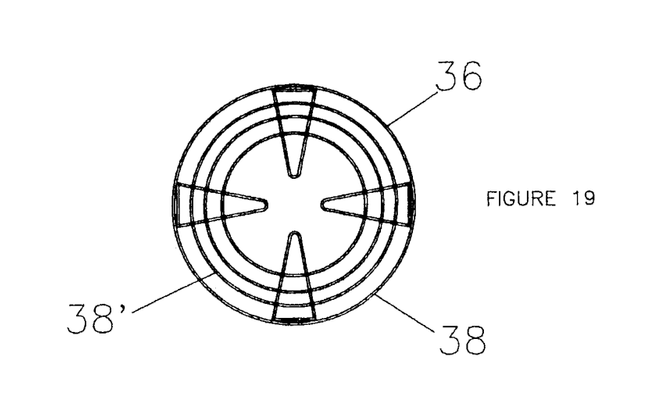
FIG. 19 is a top plan view of the cylindrical shaped embodiment of the invention as shown in FIG. 2.
Figure 20:
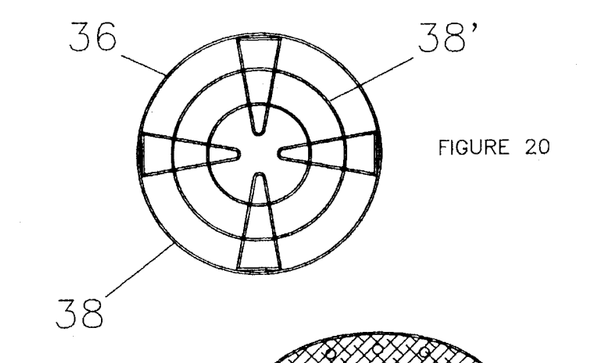
FIG. 20 is a top plan view of the wire basket component of the conical shaped embodiment of the invention as shown in FIG. 3.
Figure 21:
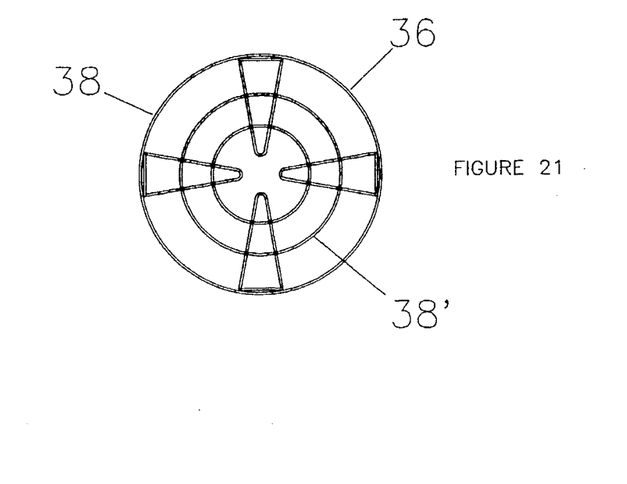
FIG. 21 is a top plan view of the wire basket component of the arcuate shaped, bullet nosed embodiment of the invention as shown in FIG. 4.

The vessel 14 can be impregnated with the root inhibiting carbon bound material 16 or preferably, the root inhibiting carbon bound material 16 is contained in a plurality of studs 28 that are disposed in a discrete pattern relationship on the inner surface 22, 22' of the walls 16, 16' and the base 18 as best seen in FIG. 7.

An arcuate collar 30 having resistance to ultraviolet breakdown is attached to an upper edge 32 of the sidewalls 16, 16' of the vessel 14. The collar 30 is disposed above the surface of the earth and surrounds the cavity. A portion 34 of the collar 30 is disposed above the surface of the ground and allows for rapid identification and ease of handling of the vessel 14 by nursery personnel when performing field tasks in the nursery.

A cradle 36 has a cooperative cross section with the vessel 14 and is adapted for congruent residence inside the vessel 14 in a vertical orientation. The cradle 36 is in removable engagement with the sidewalls 16, 16' and the base 18 of the vessel 14 for easy, damage free insertion and removal of the plant at any desired stage of growth. The cradle 36 also has a plurality of rings 38, 38' horizontally disposed in a spaced apart relationship. The topmost ring 40 has a plurality of lifting ears 42, 42' thereof adapted for engagement with conventional non-illustrated lifting means for removing the plant safely when desired. Preferably, the cradle 36 is fabricated from a metallic material, for example steel, and forms a rigid open wire frame 44. Although less preferred, the cradle 36 can be fabricated from a rope webbing material that forms a flexible open webbed frame.

Figure 5:
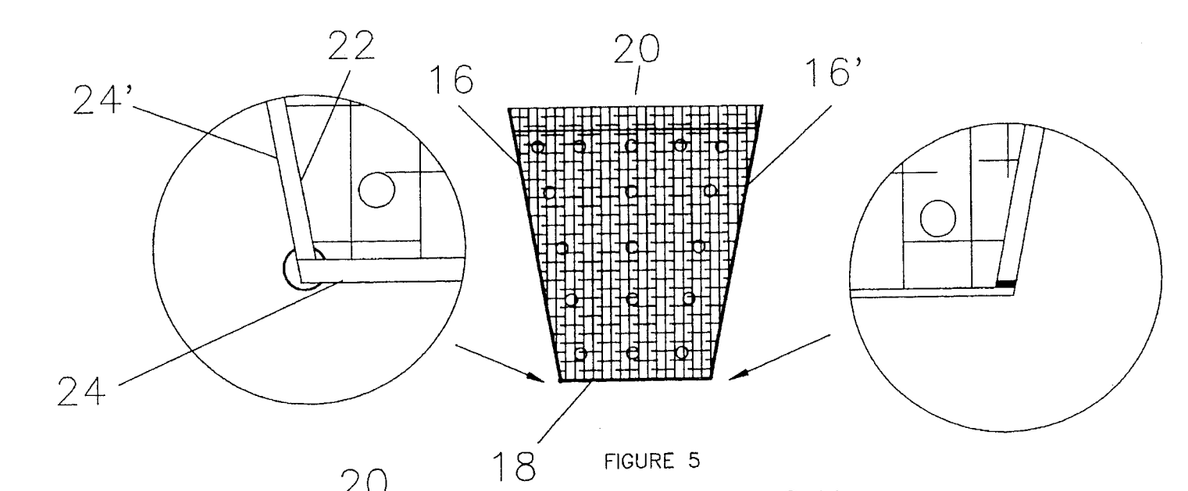
FIG. 5 is a front elevational view of the invention showing the geotextile fabric being attached at the intersection of the base and the sidewalls, the left-hand balloon showing the stitching method, and the right-hand balloon showing the gluing method.
Figure 6:
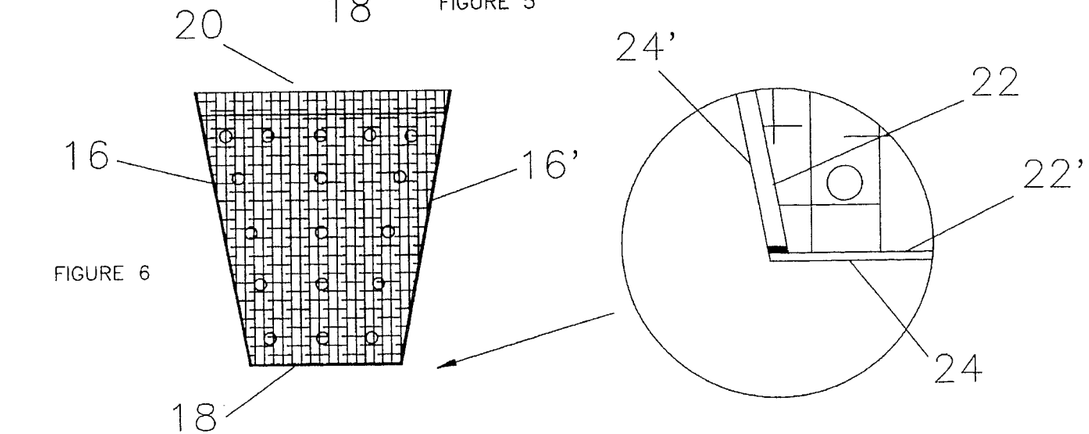
FIG. 6 is a front elevational view of the preferred embodiment of the invention showing the geotextile fabric with the spaced apart chemically impregnated nodules, and the balloon in 6 shows the gluing or seaming method of attachment used for joining the sidewall and base of the invention with the sidewall having a greater thickness than the base material.

As best seen in FIG. 5-6, the sidewalls 16, 16' and the base 18 can be joined with any suitable attachment method, but preferably the sidewalls 16, 16' are joined to the base 18 with stitching for maintaining the integrity of the vessel 14 in the cavity in the earth. A less preferred joining method is glueably adhering or hot seaming the sidewalls 16, 16' to the base 18. Likewise, the preferred method of joining the sidewalls 16, 16' to the arcuate collar 30 is with stitching along the upper edge 32 of the vessel 14. A less preferred method is gluably adhering or hot seaming the sidewalls 16, 16' to the arcuate collar 30 along the upper edge 32 of the vessel 14.

As best seen in FIGS. 1–4, the vessel 14 and cradle 30 can be made up in many geometric shapes. For example, the vessel 14 and the cradle 30 can have a cylindrical shape, an inverted pyramidal shape, a trapezoidal shape, or a bullet nose shape. The preferred shape is cylindrical.

Any suitable carbon bound material that controls root growth can be utilized in the system. For example trifuralin, oryzalin, dichlobenil, oxadiazon, and metalachlor are suitable. However, the preferred root inhibiting carbon bound material is trifluralin.

Trifluralin is sold by Dowelanco Company of Indianapolis, Ind. and is sold under the brand of Treflan. Oryzalin is also manufactured by Dowelanco Corporation and is marketed under the brand name of Sunflan. Dichlobenil is manufactured by Uniroyal Corporation of Raleigh, N.C. and is marketed under the brand name Casoron. Oxadiazon is manufactured by Rnone-Poulenc of Triangle Park, N.C. and is marketed under the name Ronstar. Metalachlor is manufactured by Ciba-Geigy of Greensboro, N.C. and is marketed under the name Pennant.

The vessel 14 should be made from a material that does not react with the chemicals in the soil and disintegrate. It has been found that a geotextile material fabricated from a non-biodegradable substance is best suited for long term residence below ground, preferably a geotextile material made from polyethylene or another thermoplastic material. The vessel 14 can be formed from either a flexible or a rigid material. The preferred material for below ground operations is flexible. The preferred material for above ground operations is rigid.

Figure 22:
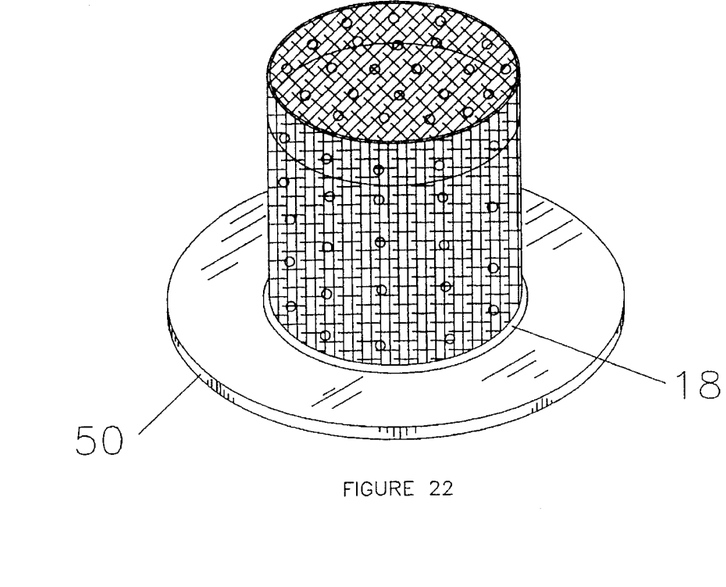
FIG. 22 is a perspective illustration of the invention having the retainer plate attached to a bottom surface thereof.
Figure 23:
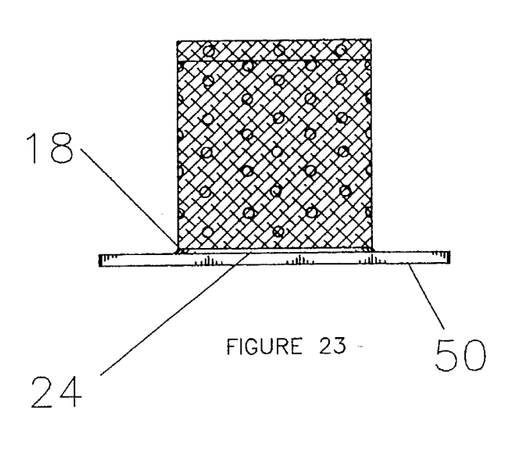
FIG. 23 is a front plan view of the invention as disclosed in FIG. 22.
Figure 24:
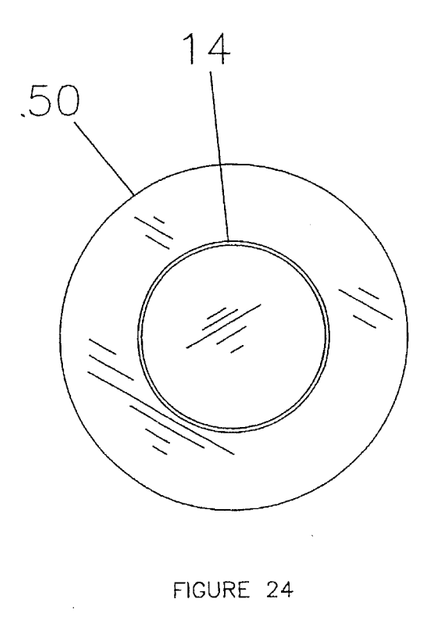
FIG. 24 is a top plan view of the invention as disclosed in FIG. 22.
Figure 25:
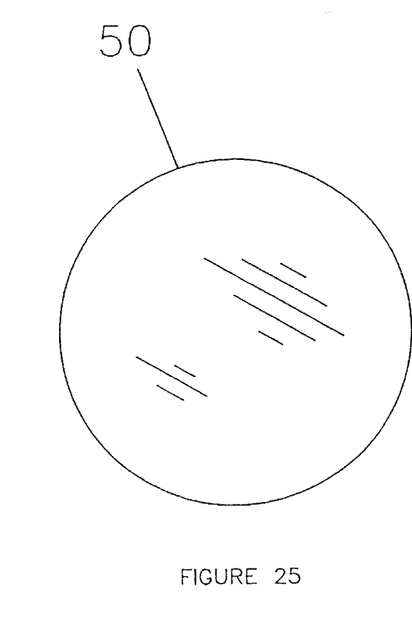
FIG. 25 is a bottom plan view of the invention as disclosed in FIG. 22.
Figures 26, 27, 28, 29:
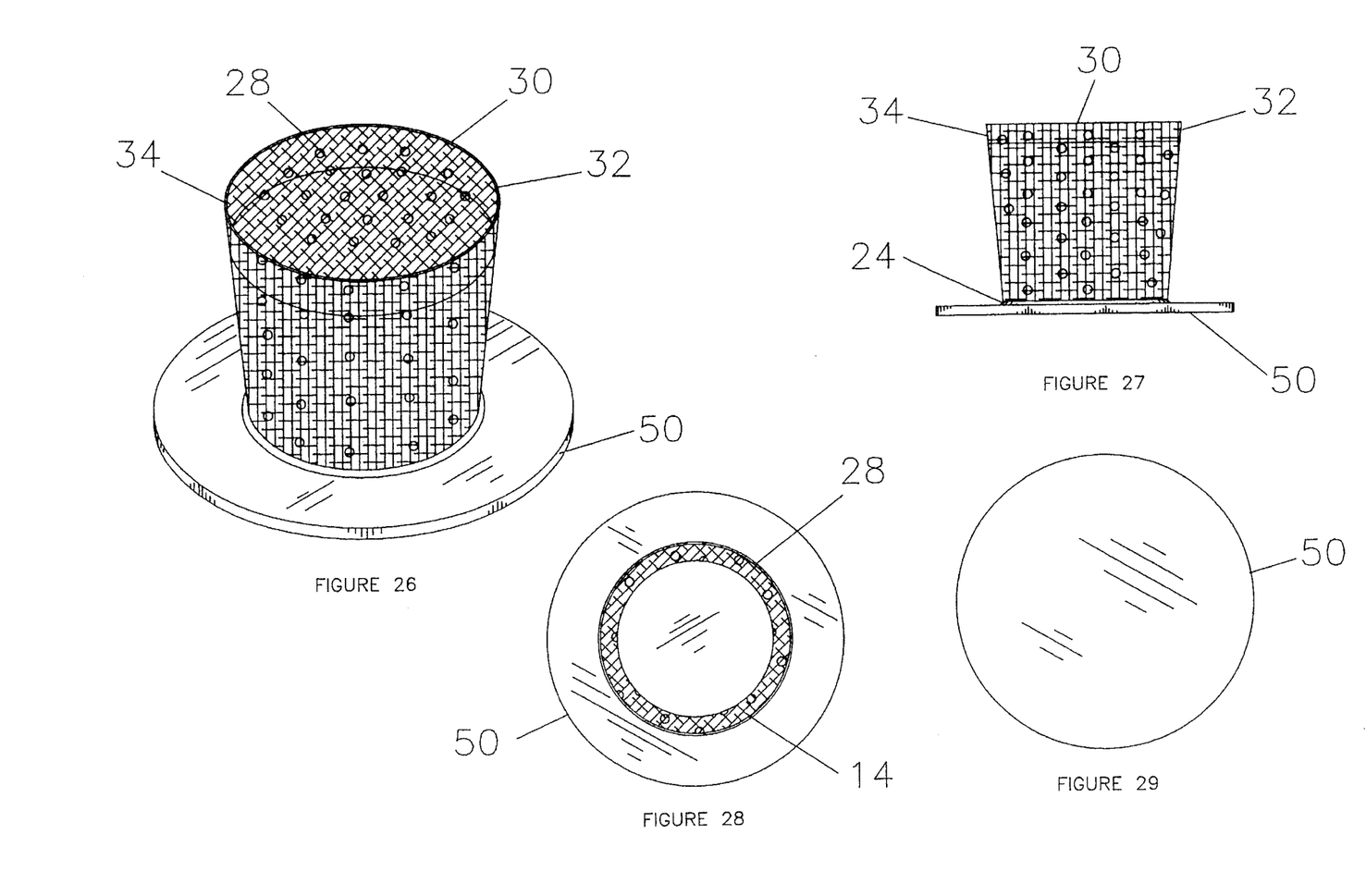
FIG. 26 is a perspective illustration of the trapezoidal vessel having the flat arcuate retainer plate attached therebelow.
FIG. 27 is a front elevation view of the invention as disclosed in FIG. 26.
FIG. 28 is a top plan view of the invention as disclosed in FIG. 26.
FIG. 29 is a bottom plan view of the invention as disclosed in FIG. 26.
Figure 30:
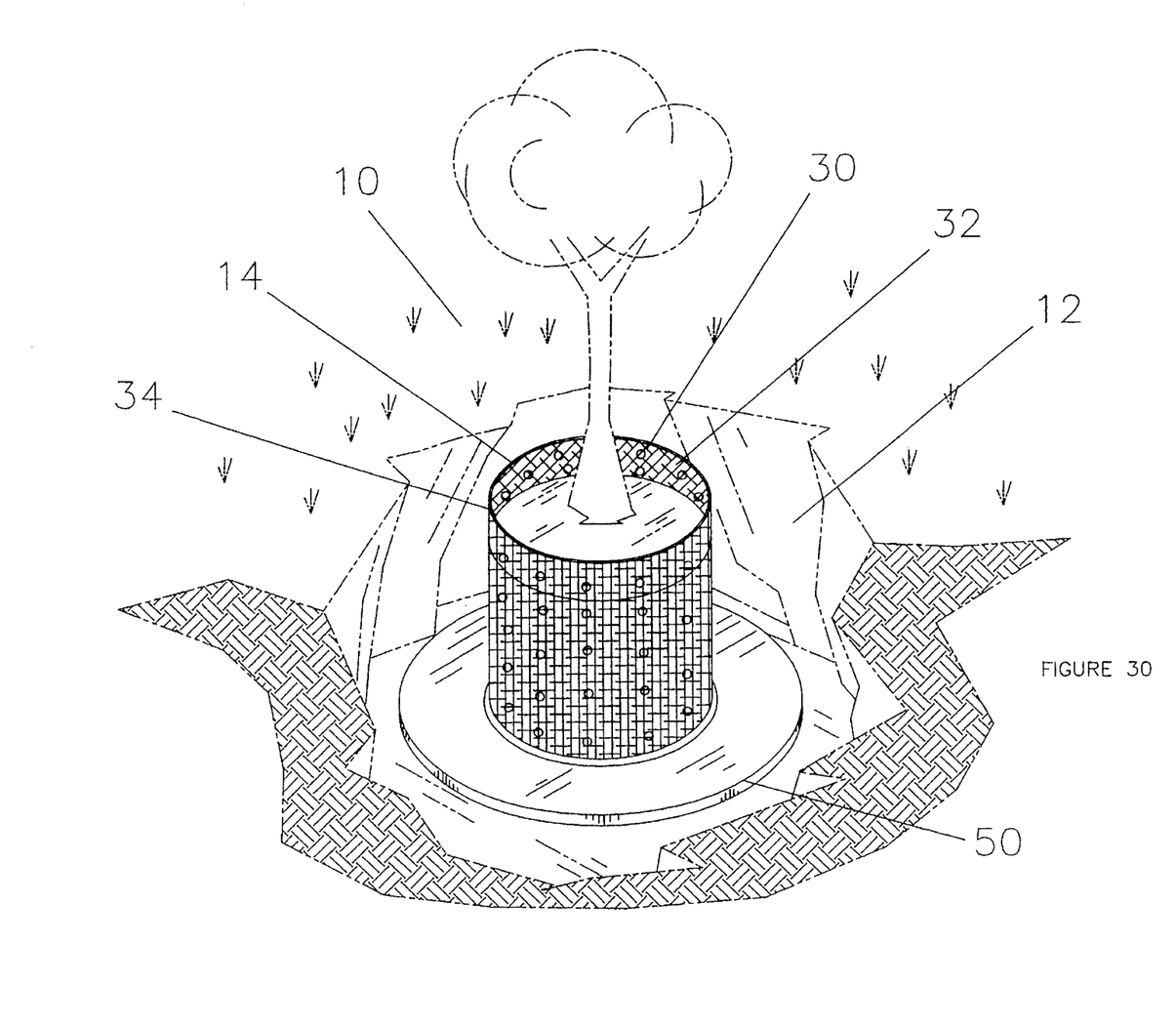
FIG. 30 is a perspective illustration of the invention as disclosed in FIG. 22 in use and operation having a tree planted therein.

A second embodiment of the invention 10 incorporates a retainer plate 50 for imparting stability to the vessel 14 when above ground and not installed in the cavity in the earth. The retainer plate 50 has a generally arcuate shape and is horizontally disposed therebeneath the base 18. Further, the plate 50 is in rigid attachment to the outer surface 24 of the base 18 and keeps the vessel 14 stationary on the earth when the plant and the cradle 36 are removed from the system. Also, the second embodiment of the invention can be utilized in above ground nursery operations when soil conditions and other factors preclude plant growth below the surface of the earth. The retainer plate 50 can be formed from any rigid material, for example plastic or metal, preferably metal.

Also, the plate 50 maintains the invention in a stable condition when extracting the root ball from the vessel 14.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of structures and the combination and arrangement of parts may be resorted to without departing from the spirit and scope of the invention.

Now that the invention has been described.

What is claimed is:

1. A root control and containment system for holding and growing a plant in a cavity in the earth for controlling vertical and horizontal root growth comprising in combination:

a vessel having upstanding sidewalls and a base therebelow and an open top thereabove, the sidewalls and base having a smooth inner and outer surface;

a root inhibiting carbon bound material in chemical communication with the vessel for storing and releasing the root inhibiting carbon bound materials over protracted periods of time for rejecting lateral root growth therethrough the wall and rejecting vertical root growth therethrough the base of the vessel; and an arcuate collar being attached to an upper edge of the sidewall of the vessel for resisting ultraviolet breakdown and being disposed above the surface of the earth surrounding the cavity for rapid identification of the cavity by field personnel when performing field tasks in the nursery.

2. A root control and containment system as recited in claim 1 and further including a cradle adapted for congruent residence inside the vessel and being in removal engagement with the sidewalls and the base of the vessel, the cradle being vertically configured and having a plurality of rings horizontally disposed in a spaced apart relationship and further having a plurality of lifting ears on an upper ring thereof for removing the plant safely when desired.

3. A root control and containment system as recited in claim 1 wherein the root inhibiting carbon bound material further includes a plurality of studs disposed in a discrete pattern relationship on an inner surface of the sidewalls and the base.

4. A root control and containment system as recited in claim 1 wherein the sidewalls are joined to the base with stitching for maintaining the integrity of the vessel in the cavity in the earth.

5. A root control and containment system as recited in claim 1 wherein the sidewalls are glueably adhered to the base for maintaining the integrity of the vessel in the cavity in the earth.

6. A root control and containment system as recited in claim 1 wherein the cradle is fabricated from a metallic material for forming an open wire frame.

7. A root control and containment system as recited in claim 1 wherein the sidewalls are joined to the arcuate collar with stitching along an upper edge thereof for urging rapid identification of the size of the vessel by nursery personnel when performing field tasks in the nursery.

8. A root control and containment system as recited in claim 1 wherein the sidewalls are gluably adhered to the arcuate collar along an upper edge thereof for urging rapid identification of the size of the vessel by nursery personnel when performing field tasks in the nursery.

9. A root control and containment system as recited in claim 1 wherein the cradle is fabricated from a rope webbing material for forming a flexible open webbed frame.

10. A chemical root control and containment system as recited in claim 1 wherein the vessel and the cradle have a cylindrical shape.

11. A chemical root control and containment system as recited in claim 1 wherein the vessel and the cradle have an inverted pyramidal shape.

12. A chemical root control and containment system as recited in claim 1 wherein the vessel and the cradle have a trapezoidal shape.

13. A chemical root control and containment system as recited in claim 1 wherein the vessel and the cradle have a bullet nose shape.

14. A chemical root control and containment system as recited in claim 1 wherein the vessel is fabricated from a geotextile material.

15. A chemical root control and containment system as recited in claim 1 wherein the cradle is fabricated from a rigid material, preferably steel.

16. A chemical root control and containment system as recited in claim 1 wherein the root inhibiting carbon bound material stored and released is trifluralin.

17. A chemical root control and containment system as recited in claim 1 wherein the root inhibiting carbon bound material stored and released is oryzalin.

18. A chemical root control and containment system as recited in claim 1 wherein the root inhibiting carbon bound material stored and released is dichlobenil.

19. A chemical root control and containment system as recited in claim 1 wherein the root inhibiting carbon bound material stored and released is oxadiazon.

20. A chemical root control and containment system as recited in claim 1 wherein the root inhibiting carbon bound material stored and released is metalachlor.

21. A chemical root control and containment system as recited in claim 1 wherein the geotextile material is fabricated from a non-biodegradable substance, preferably polyethylene or other thermoplastic material.

22. A chemical root control and containment system as recited in claim 1 wherein the cavity is disposed in a hole in the earth.

23. A chemical root control and containment system as recited in claim 1 and further including a retainer plate having a generally arcuate shape and being horizontally disposed therebeneath the base, and further being in rigid attachment to an outer surface of the base, the retainer plate for keeping the vessel stationary on the earth when the system is removed from the cavity in the earth.

24. A chemical root control and containment system as recited in claim 1 and further including a retainer plate having a generally arcuate shape and being horizontally disposed therebeneath the base, and further being in rigid attachment to an outer surface of the base, the retainer plate for keeping the vessel stationary in the earth for keeping the system stable when the plant is removed therefrom.

25. A chemical root control and containment system as recited in claim 24 wherein the vessel is disposed above the ground when growing plant stock due to adverse soil conditions.

26. A chemical root control and containment system as recited in claim 1 wherein the vessel is formed from a flexible material.

27. A chemical root control and containment system as recited in claim 1 wherein the vessel is formed from a rigid material.

28. A chemical root control and containment system as recited in claim 24 wherein the retainer plate is formed from a rigid material, preferably metal.

29. A chemical root control and containment system as recited in claim 1 wherein the size of arcuate collar indicates the age of the tree.

30. A chemical root control and containment system as recited in claim 1 wherein the arcuate collars further include a plurality of colors for indicating the species of the respective tree planted therein.

* * * * *